United States Patent [19]

Ogawa et al.

[11] Patent Number: 4,963,243

[45] Date of Patent: Oct. 16, 1990

[54] MEDIUM FOR ELECTROPHORESIS

[75] Inventors: Masashi Ogawa, Saitama; Hisashi Shiraishi; Teppei Ikeda, both of Kanagawa, all of Japan

[73] Assignee: Director of The Finance Division Minister's Secretariat Science and Technology Agency, Tokyo, Japan

[21] Appl. No.: 483,317

[22] Filed: Feb. 21, 1990

Related U.S. Application Data

[63] Continuation of Ser. No. 300,710, Jan. 23, 1989, abandoned, which is a continuation of Ser. No. 157,159, Feb. 16, 1988, abandoned, which is a continuation of Ser. No. 54,034, May 22, 1987, abandoned, which is a continuation of Ser. No. 805,575, Dec. 5, 1985, abandoned, which is a continuation of Ser. No. 568,748, Jan. 6, 1984, abandoned.

[30] Foreign Application Priority Data

Jan. 8, 1983 [JP] Japan ................................. 58-1323

[51] Int. Cl.$^5$ .................................................. B01K 5/00
[52] U.S. Cl. ............................... 204/299 R; 204/182.8
[58] Field of Search ........................ 204/299 R, 182.8

[56] References Cited

U.S. PATENT DOCUMENTS

| | | | |
|---|---|---|---|
| 3,497,437 | 2/1970 | Louderback et al. | 204/180 G |
| 4,189,370 | 2/1980 | Boschetti | 204/180 G |
| 4,319,975 | 3/1982 | Cook | 204/180 G |
| 4,415,428 | 11/1983 | Nochumson et al. | 204/180 G |

FOREIGN PATENT DOCUMENTS 0681362  8/1979  U.S.S.R. ......................... 204/180 G

OTHER PUBLICATIONS

Gelfi, C., et al., "Polymerizatioln Kinetics of Polyacrylamide Gels I. Effect of Different Crosslinkers", *Electrophoresis*, vol. 2, 1981, pp. 213–219.

Gelfi, C., et al., "Polumerization Kinetics of Polyacrylamide Gels II. Effect of Temperature", *Electrophoresis*, vol. 2, 1981, pp. 220–228.

*Primary Examiner*—Donald R. Valentine
*Attorney, Agent, or Firm*—McAulay Fisher Nissen & Goldberg

[57] ABSTRACT

In a medium for electrophoresis comprising a polyacrylamide gel formed by crosslinking polymerization of an acrylamide compound and a crosslinking agent in the presence of water, and a modifier, the improvement in which the medium contains a water-soluble polymer and agarose.

10 Claims, No Drawings

MEDIUM FOR ELECTROPHORESIS

This is a continuation of application Ser. No. 300,710, filed Jan. 23, 1989, now abandoned, which in turn is a continuation of application Ser. No. 157,159, filed Feb. 16, 1988, now abandoned, which, in turn, is a continuation of application Ser. No. 054,034, filed May 22, 1987, now abandoned, which, in turn, is a continuation of application Ser. No. 805,575, filed Dec. 5, 1985, now abandoned, which, in turn is a continuation of application Ser. No. 568,748, filed Jan. 6, 1984, now abandoned.

BACKGROUND OF THE INVENTION

1. Field of the Invention

This invention relates to a medium for gel electrophoresis (hereinafter referred to as "gel medium") used to determine base sequence of DNA, DNA fragment and DNA derivative, and in particular provides a composition of gel medium to improve workability of the medium.

2. Description of Prior Arts

In the method for determination of the base sequence of DNA, RNA, their fragments, and their derivatives according to the post-label method, the operation of slab electrophoresis using a polyacrylamide gel membrane becomes essential. The polyacrylamide membrane used for this purpose is obtainable, for instance, by a crosslinking polymerization between approx. 95 parts by weight of a monomer such as acrylamide and approx. 5 parts by weight of a bifunctional crosslinking agent such as N,N'-methylenebisacrylamide in an aqueous solution containing a mixture of the monomer and the crosslinking agent and a polymerization initiator (hereinafter referred to as "gel forming solution").

Recently, as the study concerning the gene has progressed, a rapid operation for determination of DNA base sequence is required. The electrophoresis using the polyacrylamide as the electrophoresis medium layer becomes almost essential for performing the determination of DNA base sequence, because the polyacrylamide medium gives prominently high resolution.

However, the conventional polyacrylamide gel membrane has a serious disadvantage that the membrane is brittle and easily breakable. Therefore, a polyacrylamide gel membrane for determination of DNA base sequence is generally prepared by a process in which a gel forming solution is poured into a cell formed with two glass plates (having a certain space with thickness of 0.3 to 1 mm) to prepare a gel membrane in the cell. To the gel membrane, sample inlets must be provided so that the membrane can receive DNA samples (Maxam-Gilbert decomposed $^{32}$P-labeled DNA or etc.). Accordingly, a sample slot former is generally inserted into the cell after the gel forming solution is poured therein but before gelation takes place, so that the sample slots can be provided to the gel membrane. It is difficult to cut off the edge from a prepared membrane with a razor or the like to provide the sample inlets, because the gel membrane is very brittle and easily breakable, as descirbed above. For this reason, the above mentioned process involving the provision of sample slots by insertion of the sample slot former in advance of the gelation is utilized. This complicated process is a serious obstacle in producing the polyacrylamide gel membrane on a mass scale.

The polyacrylamide gel membrane prepared as above is then kept vertically together with the glass plates, and the sample slot former is removed. A certain amount of a sample (Maxam-Gilbert decomposed $^{32}$P-labeled DNA or etc.) is poured into the sample slots, and the sample is electrophoresed. The electrophoresis is continued for a certain period of time, one glass plate is removed carefully, and the autoradiographic process is performed on the gel membrane. Thereafter, the determination of DNA base sequence is carried out. Even in this process, the gel membrane sometimes breaks when the glass plate is removed, because the conventional gel membrane is very brittle. Thus, the brittleness of the conventional membrane is a very serious problem.

SUMMARY OF THE INVENTION

An object of the present invention is to provide a medium for electrophoresis which is improved in the unfavorable feature such as brittleness of the conventional polyacrylamide gel membrane for determination of DNA base sequence, in which the unfavorable feature stems mainly from the composition of the gel medium.

Another object of the invention is to provide a polyacrylamide gel medium which is satisfactory in electrophoretic characteristics such as resolution and migration velocity, being free from brittleness, easy to handle, capable of being cut into a desired shape, and usable for producing a gel column to be employed in the disk electrophoresis if required. This means that the medium for electrophoresis provided by the invention is remarkably excellent in total characteristics including the function as molecular sieve, as compared with the conventional medium.

There is provided by the present invention a medium for electrophoresis comprising a polyacrylamide gel formed by crosslinking polymerization of an acrylamide compound and a crosslinking agent in the presence of water, and a modifier, which is characterized in that said medium contains a water-soluble polymer and agarose.

DETAILED DESCRIPTION OF THE INVENTION

Examples of the acrylamide compound employable in the invention include acrylamide and its homologues such as acrylamide, N-methylacrylamide, N,N-dimethylacrylamide, N-(hydroxymethyl)acrylamide, and diacetonacrylamide, and these acrylamide homologues may be employed independently or in combination. Acrylamide is most preferable among these acrylamide compounds, and said acrylamide can be also preferably employed in combination with one or more of other acrylamide compounds.

As the crosslinging agent used to obtain the polyacrylamide gel of the invention, a crosslinking agent described in "Electrophoresis" 1981, 2, 220–228, or known as such may be employed. Examples of the crosslinking agent include bifunctional compounds such as N,N'-methylenebisacrylamide (BIS), N,N'-propylenebisacrylamide (PBA), diacrylamide dimethylether (DAE), 1,2-diacrylamide ethyleneglycol (DEG), ethylenureabisacrylamide (EUB), ethylene diacrylate (EDA), N,N'-diallyltartardiamide (DATD), and N,N'-bisacrylylcystamine (BAC). The crosslinking agent can be employed in an amount of approx. 2 to 30 wt. %, preferably approx. 3 to 10 wt. %, based on the total weight of the monomer (i.e., acrylamide compound) and the crosslinking agent.

As the modifier, a compound containing at least one carbamoyl group can be used. Examples of the modifier include urea and formamide. Urea is most preferred. The modifier can be used in an amount of approx. 40 to 60 wt. % based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

As the water-soluble polymer, a water-soluble polymer of the addition polymerization type or condensation polymerization type can be used. Examples of the polymer of the addition polymerization type include nonionic water-soluble polymers such as polyvinyl alcohol, polyvinyl pyrrolidone, and polyacrylamide. Examples of the polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 50 wt. %, preferably, approx. 5 to 30 wt. %, based on the total weight of the monomer and crosslinking agent.

According to the present invention, the addition of a water-soluble polymer serves to impart elasticity to the gel medium, and thus modified gel medium is still elastic even if it is dried. Thus, the gel medium is so improved as to be free from the brittleness, whereby the gel medium becomes hardly breakable. Further, the viscosity of the gel medium can be controlled by selecting the molecular weight and amount of the water-soluble polymer.

There is no specific limitation on agarose to be included to the gel medium of the invention, and any type of agarose such as agarose of the low electric penetration type, the medium electric penetration type, or high electric penetration type can be used. Examples of agarose employable in the invention include agaroses disclosed in Japanese Patent Provisional Publication Nos. 55(1980)-5730, 55(1980)-110946 (corresponding to USP 4,290,911 and GB 2 042 571A), 57(1982)-502098 (WO 82/02599), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel forming solution can be controlled through changing the temperature of the solution.

A pH buffer agent can be contained in the gel medium of the invention. Any buffer agent which is able to buffer a solution to a range of pH 8.0 to 9.0, preferably pH 8.2 to 8.3 can be used. Buffer agents employable in the invention are described in publications such as "Chemistry Handbook, Fundamental Edition" compiled by The Chemical Society of Japan (Maruzen Ltd., Tokyo, 1966) pages 1312–1320; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include tris (hydroxymethyl)aminomethane (Tris), N,N-bis(2-hydroxyethyl)glycine (Bicine), Na or K salt of N-2-hydroxyethylpiperazine-N'-2-hydroxypropane-3-sulfonic acid and Na or K salt of N-[tris(hydroymethy)methyl]-3-aminopropanesulfonic acid, and further acids, alkalis, or salts employable together with any of these buffer agents. Preferred examples of the buffer agent include Tris, and the combination of boric acid and EDTA 2Na salt (pH 8.2).

In the case that the gel medium of the invention is used in the form of layer or membrane, a gel layer or gel membrane can be prepared by a process in which a gel forming solution is coated by a known method on an electric insulation support having a smooth hydrophilic surface, and the gel forming solution is crosslinked to polymerization thereon. Examples of the support include glass plate, hydrophilic polymers in the form of plate or sheet, and other polymers (e.g., polyethylene terephthalate, polycarbonate of bisphenol A, polyvinyl chloride, vinylidene chloride - vinyl chloride copolymer, polymethylmethacrylate, polyethylene, polypropylene, cellulose acetate, and cellulose acetate propionate) in the form of plate or sheet, a surface of which is made hydrophilic by a known surface treatment. Examples of the treatment employable to make the surface of these polymers hydrophilic include known methods such as irradiation with ultra-violet rays, glow discharge treatment, corona discharge treatment, flame treatment, electron beam treatment, chemical etching, or electrochemical etching.

In the case that the gel forming solution is crosslinked to polymerization on the surface of the support, the surface of the gel forming soultion can be covered with a cover film, sheet, or plate. The same material as employable for the support can be employed as the cover film, sheet, and plate.

The gel medium used in the invention is formed by radical crosslinking-polymerization between the monomer such as acrylamide with the bifunctional compound (crosslinking agent) in an aqueous solution in which the water soluble polymer and agarose are dissolved almost homogeneously. The gel is assumed to have a structure in which the water-soluble polymer and agarose are dispersed in the three dimensional crosslinked polymer, and the water-soluble polymer chains entangle with the three dimensional crosslinked polymer chains. This structure is one of the characteristic features of the gel medium of the invention.

The crosslinking polymerization can be initiated in the presence of a peroxide and/or under irradiation of ultra-violet rays. The reaction can be further accelerated by heat and irradiation with ultra-violet rays.

As the polymerization catalyst, a known low temperature-polymerization initiator can be used. Examples of the initiator include a mixture of N,N,N',N'-tetramethylethylenediamine and ammonium persulfate, and a combination of a mixture of N,N,N',N'-tetramethylethylenediamine, riboflavin and hydrogen peroxide and irradiation with ultra-violet rays.

A polyol compound such as glycerol or ethylene glycol can be contained in the gel medium of the invention as a wetting agent. The polyol compound can be introduced in an amount of approx. 5 to 40 wt. % based on the volume of the aqueous gel medium. Glycerol is particularly preferable among polyol compounds.

The present invention will be more clearly understood with reference to the following examples, but these examples are by no means understood to restrict the invention.

EXAMPLE 1

A glass plate cell with thickness of 0.5 mm was constructed using two glass plates with smooth surface and spacer with thickness of 0.5 mm. The acrylamide gel composition solution (gel forming solution) set forth in Table 1 was poured into the cell and crosslinked to polymerization to form a polyacrylamide gel membrane. One glass plate was removed after gelation was complete, and sample slots were provided by cutting the polyacrylamide gel membrane by means of a sharp cutter.

TABLE 1

| | Gel Composition | | | |
|---|---|---|---|---|
| | Sample Number | | | |
| | 1 | 2 | 3 | 4 |
| Gel Composition | | | | |
| Acrylamide | 11.87 g | 11.87 g | 11.87 g | 11.87 g |
| N,N'-Methylenebis-acrylamide | 0.63 g | 0.63 g | 0.63 g | 0.63 g |
| Urea | 42 g | 42 g | 42 g | 42 g |
| Solid Agarose | None | 0.3 g | 0.3 g | 1.0 g |
| Solid Polyacrylamide | None | 1.25 g | 2.5 g | 1.25 g |
| Tris(hydroxymethyl)-aminomethane | 1.08 g | 1.08 g | 1.08 g | 1.08 g |
| Boric acid | 0.55 g | 0.55 g | 0.55 g | 0.55 g |
| EDTA.2Na | 93 mg | 93 mg | 93 mg | 93 mg |
| Water | (added to make 100 ml) | | | |
| Polymerization Initiator | | | | |
| Ammonium persulfate (5 wt. %) | 1.3 ml | 1.3 ml | 1.31 ml | 1.3 ml |
| N,N,N',N'-tetramethyl-ethylenediamine | 33 μl | 33 μl | 33 μl | 33 μl |

Remark: A combination of tris(hydroxymethyl)aminomethane, boric acid and EDTA.2Na is a buffer composition showing a buffering capacity to make pH 8.2

As for Sample No. 1 (reference gel membrane), the cut end was cracked and the membrane was broken, and accordingly sample slots of sharp edge could not be obtained. On the other hand, as for Samples Nos. 2 to 4 (gel membrane according to the invention), sample slots showing sharp edge were easily obtained.

The gel membrane obtained as above was again covered with a glass plate again, and the electrophoresis was performed by the conventional method to observe the electrophoresed dye pattern.

As for Sample No. 1, serious disorder of the electrophoresed dyes was observed. On the other hand as for Samples Nos. 2 to 4, no disorder was observed, and a uniform electrophoresed pattern was obtained.

Accordingly, it is apparent that the problem in brittleness of the gel membrane is remarkably improved by the present invention, as compared with the conventional gel membrane.

EXAMPLE 2

Gel membranes were prepared using the same gel compositions as described in Example 1. For reference, a membrane was prepared from the same composition as that of Sample No. 1, except that a sample slot former was employed for the preparation of the sample slots (Sample No. 1-A: reference gel membrane).

The experiment for the DNA base sequence determination was performed using these gel membranes and a sample prepared from $^{32}P$ labeled DNA decomposed by Maxam-Gilbert method.

Sample No. 1-A and Sample Nos. 2 to 4 exhibited normal electrophoresed patterns and the DNA base sequence could be determined with no difficulty, but Sample No. 1 exhibited a disordered electrophoresed pattern.

Accordingly, it is apparent that the gel membrane according to the present invention exhibits satisfactory electrophoresis characteristics, being free from the brittleness.

EXAMPLE 3

A polyacrylamide gel membrane was prepared in the same manner as in Example 1 except that the solid polyacrylamide (water-soluble polymer) was replaced with polyethylene glycol (average molecular weight: 20,000). Thus prepared membrane was subjected to the same electrophoresis. It was observed that the gel membrane exhibited satisfactory electrophoresis characteristics, as well as that the brittleness of membrane was remarkably improved and the gel membrane was freely cut for the formation of sample slot.

Accordingly, the advantage of the invention was confirmed.

We claim:

1. In a medium for electrophoresis comprising a polyacrylamide gel formed by crosslinking polymerization of an acrylamide compound and a crosslinking agent in the prsence of water and a compound containing at least one carbamoyl group as a modifier, the improvement which comprises the polyacrylamide gel containing a water-soluble polymer and agarose, said water-soluble polymer in the form of a polymer and agarose, being incorporated into the gel, the water-soluble polymer being present in an amount in the range of 2 to 50 wt. % based on the total weight of the acrylamide compound and crosslinking agent, and the amount of said agarose being in the range of 0.1 to 2 wt/v percent based on the volume of the polyacrylamide gel.

2. The medium for electrophoresis as claimed in claim 1 wherein said crosslinking agent is present in the range of 2 to 30 wt. % based on the total weight of the acrylamide compound and crosslinking agent and said modifier is present in the range of 40 to 60 wt/v percent based on the volume of the polyacrylamide gel.

3. The medium for electrophoresis as claimed in claim 2 wherein said water-soluble polymer is present in the range of 5 to 30 wt. % based on the total weight of the acrylamide compound and crosslinking agent, said agarose is present in the range of 0.3 to 1.2 wt/v percent based on the volume of the polyacrylamide gel, and said crosslinking agent is present in the range of 2 to 30 wt. % based on the total weight of the acrylamide compound and crosslinking agent.

4. The medium for electrophoresis as claimed in claim 1 or 2, in which said modifier is urea or formamide.

5. The medium for electrophoresis as claimed in claim 4 wherein said modifier is urea and the amount of said urea is from approximately 7 moles to the saturation amount per one liter of the aqueous gel containing the acrylamide compound and crosslinking agent.

6. The medium for electrophoresis as claimed in claim 1 or 2, in which said medium is a membrane having a substantially even thickness provided on a smooth surface of a support.

7. The medium for electrophoresis as claimed in claim 1 or 2 wherein said water-soluble polymer is selected from the group consisting of water-soluble polyacrylamide having a molecular weight of 10,000 to 1,000,000, and water-soluble polyethylene glycol having a molecular weight of 10,000 to 1,000,000.

8. The medium for electrophoresis as claimed in claim 1 or 2 wherein said medium further contains a pH buffer agent capable of buffering the medium to a range of pH 8.0 to 9.0.

9. The medium for electrophoresis as claimed in claim 1 or 2 wherein said acrylamide compound is selected from the group consisting of acrylamide, N-methylacrylamide, N,N-dimethylacrylamide, N-(hydroxymethyl)acrylamide and diacetoneacrylamide.

10. The medium for electrophoresis as claimed in claim 9 wherein the crosslinking agent is selected from the group consisting of N,N'-methylenebisacrylamide, N,N'-propylenebisacrylamide, diacrylamide dimethylether, 1,2-diacrylamide ethyleneglycol, ethylenureabisacrylamide, ethylene diacrylate, N,N'-diallyltartardiamide, and N,N'-bisacrylylcyatamine.

* * * * *